United States Patent [19]

Khudyakov et al.

[11] Patent Number: 5,503,995

[45] Date of Patent: Apr. 2, 1996

[54] EXCHANGEABLE TEMPLATE REACTION

[75] Inventors: Yury Khudyakov, Atlanta; Howard A. Fields, Marietta, both of Ga.

[73] Assignee: The United States of America as represented by the Department of Health & Human Services, Washington, D.C.

[21] Appl. No.: 261,670

[22] Filed: Jun. 17, 1994

Related U.S. Application Data

[63] Continuation of Ser. No. 849,294, Mar. 10, 1992, abandoned.

[51] Int. Cl.$^6$ ............................... C12P 19/34; C12Q 1/68
[52] U.S. Cl. ................... 435/91.1; 435/91.5; 435/91.52; 435/172.3; 935/17; 935/78
[58] Field of Search ................................ 435/91.1, 91.5, 435/6, 172.1, 172.3, 91.52; 935/16, 17

[56] References Cited

U.S. PATENT DOCUMENTS

| | | | |
|---|---|---|---|
| 4,521,509 | 6/1985 | Benkovic et al. | 435/6 |
| 4,672,040 | 6/1987 | Josephson | 436/526 |
| 4,965,188 | 10/1990 | Mullis et al. | 435/6 |

FOREIGN PATENT DOCUMENTS

| | | |
|---|---|---|
| 0359545 | 3/1990 | European Pat. Off. . |
| 0438292 | 7/1991 | European Pat. Off. . |
| 9000626 | 1/1990 | WIPO . |
| WO91/17267 | 11/1991 | WIPO . |
| WO92/05287 | 4/1992 | WIPO . |

OTHER PUBLICATIONS

Mandecki et al, Gene (1988) 58:101–107.
Bell et al Gene 63(1988) 155–163.
Rossi et al al J Biol Chem (1982) 257:9226–9229.
Kern et al J Biol Chem (1972) 247:311–318.
New England Biolabs Catalog, 1990–1991, p. 18.
Adams et al., "Synthesis of a gene for the HIV transactivator protein TAT by a novel single stranded approach involving in vitro gap repair," *Nucleic Acids Res.* 16:4287–4298 (1988).
Agarwal et al., "Total synthesis of the gene for an alanine transfer ribonucleic acid from yeast," *Nature* 227:27–34 (1970).
Alexander et al., "Synthesis and characterization of a recombinant myohemerythrin protein encoded by a synthetic gene," *Gene* 99:151–156 (1991).
Bell et al., "Chemical synthesis, cloning and expression in mammalian cells of a gene coding for human tissue–type plasminogen activator," *Gene* 63:155–163 (1988).
Chen et al., "A new method for the synthesis of a structural gene," *Nucleic Acids Res.* 18:871–878 (1990).

(List continued on next page.)

Primary Examiner—W. Gary Jones
Assistant Examiner—Carla Myers
Attorney, Agent, or Firm—Needle & Rosenberg

[57] ABSTRACT

The invention provides a method for the synthesis of DNA based on a cyclic mechanism of combining deoxyoligonucleotides comprising combining: (a) a series of unique single-stranded deoxypolynucleotides, each having a 5' sequence which, when in double-stranded form, can be enzymatically treated to form a unique 3' single-stranded protrusion for selective cyclic hybridization with another unique single-stranded deoxypolynucleotide of the series; (b) a unique deoxypolynucleotide having a 3' sequence which can selectively hybridize with one of the unique single-stranded deoxypolynucleotides of (a); (c) a polymerase which can direct the formation of double-stranded deoxypolynucleotides from the single-stranded deoxypolynucleotides; and (d) an enzyme which can form a unique single-stranded 3' protrusion from the double-stranded deoxypolynucleotides; under conditions which hybridize the unique single-stranded deoxypolynucleotides in a cyclic manner to form the DNA. Also provided is a kit comprising a series of unique synthesized single-stranded deoxypolynucleotides, each having a 5' sequence which, when in double-stranded form, can be enzymatically treated to form a unique 3' single-stranded protrusion for selective cyclic hybridization with another unique single-stranded deoxypolynucleotide of the series.

26 Claims, 9 Drawing Sheets

OTHER PUBLICATIONS

Ciccarelli et al, "Insertional gene synthesis: a novel method of assembling consecutive DNA sequences within specific sites in plasmids. Construction of the NIH–1 tat gene," *Nucleic Acids Research* 18:1243–1248 (1990).

Ciccarelli et al., "Construction of synthetic genes using PCR after automated DNA synthesis of their entire top and bottom strands," *Nucleic Acids Res.* 19:6007–6013 (1991).

Clark et al., "DNA synthesis on discontinuous templates by DNA polymerase I of Escherichia coli," *Gene* 104:75–80 (1991).

Denefle et al., "Chemical synthesis of a gene coding for human angiogenin, its expression in Escherichia coli and conversion of the product into its active form," *Gene* 56:61–70 (1987).

Derbyshire et al., "A simple and efficient procedure for saturation mutagenesis using mixed oligonucleotides," *Gene* 46:145–152 (1986).

Edge et al., "Total synthesis of a human leukocyte interferon gene," *Nature* 292:756–762 (1981).

Ferretti et al., "Total synthesis of a gene for bovine rhodopsin," *Proc. Natl. Acad. Sci. USA* 83:599–603 (1986).

Hayden and Mandecki, "Gene synthesis by serial cloning of oligonucleotides," *DNA* 7:571–577 (1988).

Horton et al., "Engineering hybrid genes without the use of restriction enzymes: gene splicing by overlap extension," 77:61–68 (1989).

Hostomsky et al., "Solid–phase assembly of cow colostrum trypsin inhibitor gene," *Nucleic Acids Res.* 15:4849–4856 (1987).

Jay et al., "Chemical synthesis of a biologically active gene for human immune interferon–gamma".

"Prospect for site–specific mutagenesis and structure–function studies," *J. Biol. Chem.* 259:6311–6317 (1984).

Jayaraman et al., "PCR mediated gene synthesis," *Nucleic Acids Res.* 17:4403 (1989).

Jayaraman et al., "Polymerase chain reaction–mediated gene synthesis: synthesis of a gene coding for isozyme C of horseradish peroxidase," *Proc. Natl. Acad. Sci. USA* 88:4084–4088 (1991).

Jayaraman and Puccini, "A PCR–mediated gene synthesis strategy involving the assembly of oligonucleotides representing only one of the strand," *BioTechniques* 12:392–398 (1992).

Kalman et al., "Synthesis of a gene for human serum albumin and its expression in Saccharomyces cerevisiae," *Nucleic Acids Res.* 18:6075–6081 (1990).

Khorana, "Total synthesis of a gene," *Science* 203:614–625 (1979).

Mandecki et al., "Chemical synthesis of a gene encoding the human complement fragment C5a and its expression in E. coli," *Proc. Natl. Acad. Sci. USA* 82:3543–3547 (1985).

Mandecki and Bolling, "FokI method of gene synthesis," 58:101–107 (1988).

Mazin et al., "Site–directed insertion of long single–stranded DNA fragments into plasmid DNA," *DNa and Cell. Biol.* 9:63–69 (1990).

Rink et al., "A large fragment approach to DNA synthesis: total synthesis of a gene for the protease inhibitor eglin C from the leech Hirudo medicinalis and its expression in E. Coli," *Nucleic Acids Res.* 12:6369–6387 (1984).

Rossi et al., "An alternate method for synthesis of double–stranded DNA segments," *J. Biol. Chem.* 257:9226–9229 (1982).

Scarpulla et al., "Use of a new retrieving adaptor in the clining of a synthetic human insulin A–chain gene," *Anal. Biochem.* 121:356–365 (1982).

Sproat and Gait, "Chemical synthesis of a gene for somatomedin C," *Nucleic Acids Res.* 13:2959–2977 (1985).

Talib et al., "Cloning and expression in *Escherichia coli* of a synthetic gene encoding the extra–cellular domain of the human muscle acetylcholine receptor alpha–subunit," *Gene* 98:289–293 (1990).

Terwilliger, "Construction of a synthetic variant of the bacteriophage f1 gene V, by assembling oligodeoxynucleotides corresponding to only one strand of DNA," *Gene* 71:41–47 (1988).

Uhlmann, "An alternative approach in gene synthesis: use of long selfpriming oligonucleotides for the construction of double–stranded DNA," *Gene* 71:29–40 (1988).

Weiner and Scheraga, "A method for the cloning of unpurified signle1∝stranded oligonucleotides," *Nucleic Acids Res.* 17:7113 (1989).

Wosnick et al., "Rapid construction of large synthetic genes: total chemical synthesis of two different versions of the bovine prochymosin gene," *Gene* 60:115–127 (1987).

Wosnick et al., "Total chemical synthesis and expression in *Escherichia coli* of a maize glutathione–transferase (GST) gene," *Gene* 76:153–160 (1989).

OLIGO A

5'- CCCAGATCTCAATCTCGGGAATCTCTCAATGTTAGTATTCCTTGGACTCATAAGGTGGGAA
         BglII

OLIGO B    BstXI

5'- CCCCCACCACTCTGGATTAAAGATAGGTACTGTAGAGGAAAAAAGCGCCCGTAAAGTTTC-
    CCACCTTAT

OLIGO C    ApaI

5'- CCCGGGCCCACAAATTGTTGACACCTATTAATAATGTCCTCTTGTAAATGAATCTTAGG-
    AAAGGAAGGAGTTTGCCACT

```
      BglII
      ------
5'-CCCAGATCT-----ATAAGGTGGGAA
                 TATTCCACCCTT-----GGTCTCACCACCCCC-5'
                                  --------------
                                       BstXI
```

POLYMERASE

```
5'-CCCAGATCT-----ATAAGGTGGGAA-----ccagagtggtgggggg-3'
3'-gggtctaga-----TATTCCACCCTT-----GGTCTCACCACCCCC-5'
```

BstXI

```
5'-CCCAGATCT-----ATAAGGTGGGAA-----ccagagtg-3'
3'-gggtctaga-----TATTCCACCCTT-----GGTC
``` oligo C

```
5'-CCCAGATCT-----ATAAGGTGGGAA-----ccagagtg-3'
3'-gggtctaga-----TATTCCACCCTT-----GGTC||||
                                      TCAC-----CCCGGGCCC-5'
                                                ------
                                                 ApaI
```

POLYMERASE

```
      BglII
      ------
5'-CCCAGATCT-----ATAAGGTGGGAA-----ccagagtg------gggcccggg-3'
3'-gggtctaga-----TATTCCACCCTT-----GGTC||||||||||||||||||||
                                      TCAC-----CCCGGGCCC-5'
                                                ------
                                                 ApaI
```

Fig. 3-I

NdeI

5'- CCCCATATGAGCACGATTCCTAAACCACAAAGAAAAACCAAACGTAACACCAATCGA-

CGACCACAAGATGTAAAGT (1)

BstXI

5'- CCCCCACctccGTGGAAGCAAATAGACTCCACCAACGATCTGACCGCCACCCGGGAA-

CTTTACATCTTG (2)

BstXI

5'- CCCCCATcttcCTGGTCGCGCGCACACCCAACCTAGGTCCCctcc (3)

BstXI

5'- CCCCCAAcctcGTGGTTGCGAGCGCTCGGAAGTcttc (4)

DdeI

5'- CCCCCTCAGGCCGACGCACTTTAGGGATAGGCTGTCGTCTAcctc (5)

Fig. 3-II
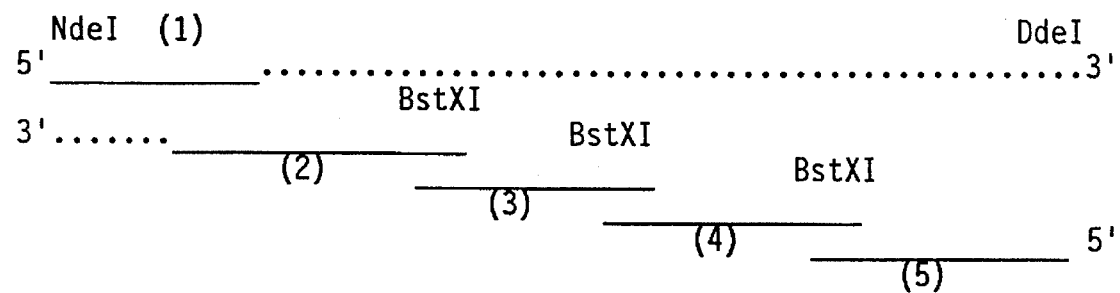

Fig. 4-I

```
        DdeI
        -------
5'- CCCCCTGAGGGCAGGACCTGGGCTCAACCCGGTTACCCCTGGCCCCTCTATGGC-

AATGAGGGCTGCGGGTGGGCG                                       (6)

BstXI
            ------------
5'- CCCCAGATCAGTGGGTCCCCAACTCGGTCGAGAGCCGCGGGGAGACAGGAGCC-

ATCCCGCCCACCCGCAG                                           (7)

ClaI
        ------
5'- CCCATCGATGACCTTACCCAAATTTCGCGACCTACGTCGCGGATCA              (8)
```

Fig. 4-II
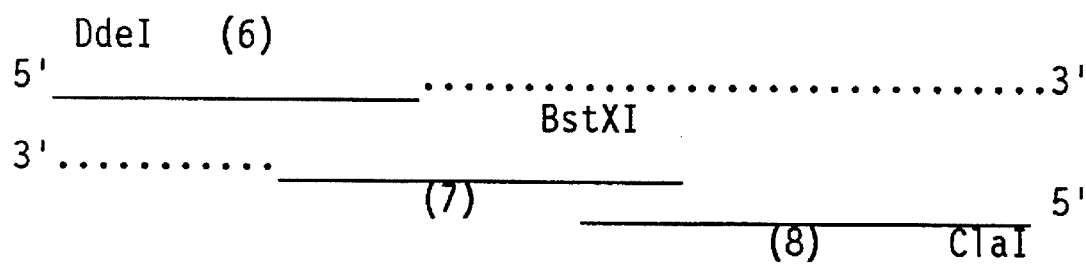

Fig. 5-I

```
        ClaI
        ------
5'-CCCATCGATACCCTCACGTGCGGCTTCGCCGACCTCATGGGGTACATACCGCTCGTC    (9)

BstXI
        ------------
5'-CCCCCAACTCCATGGGCAAGGGCTCTGGCGGCACCTCCAAGAGGGGCGCCGACGAGC-

GGTAT                                                         (10)

BstXI
        ------------
5'-CCCCCAGGAAGATGGAGAAAGAGCAACCAGGAAGGTTTCCTGTTGCATAATTGACGC-

CGTCTTCTAGAACCCGTACTCC                                        (11)

HindIII
        ------
5'-CCCAAGCTTTTAGTTTCGAACTTGGTAGGCTGAAGCGGGCACAGTCAGGCAAGAGAG-

CAGGGCCAGAAGGAAG                                              (12)
```

Fig. 5-II
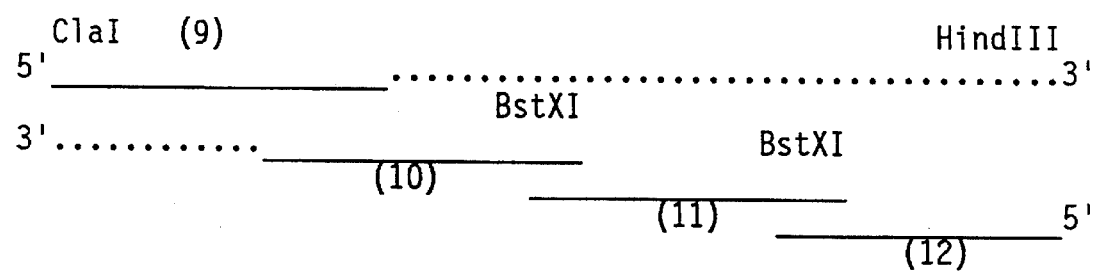

EXCHANGEABLE TEMPLATE REACTION

This application is a continuation of application Ser. No. 07/849,294, filed Mar. 10, 1992 and now abandoned.

Various references are cited herein. These references are hereby incorporated by reference into the application to more fully describe the state of the art to which the invention pertains.

BACKGROUND OF THE INVENTION

The technology for the functional expression of DNA fragments in heterologic genetic systems depends to a great extent on an accessible source of DNA. There are two ways to obtain genetic material for genetic engineering manipulations: (1) isolation and purification of DNA in an appropriate form from natural sources (this technique is well-elaborated and constitutes the backbone of genetic engineering and molecular biology), or (2) the synthesis of DNA using various chemical-enzymatic approaches, a discipline that has been intensively researched over the last 15 years. The former approach is limited to naturally-occurring sequences which do not easily lend themselves to specific modification. The latter approach is much more complicated and labor-intensive. However, the chemical-enzymatic approach has many attractive features including the possibility of preparing, without any significant limitations, any desirable DNA sequence.

Two general methods currently exist for the synthetic assembly of oligonucleotides into long DNA fragments. First, oligonucleotides covering the entire sequence to be synthesized are first allowed to anneal, and then the nicks are repaired with DNA ligase. The fragment is then cloned directly, or cloned after amplification by the polymerase chain reaction (PCR). The DNA is subsequently used for in vitro assembly into longer sequences. This approach is very sensitive to the secondary structure of oligonucleotides, which interferes with the synthesis. Therefore, the approach has low efficiency and is not reliable for assembly of long DNA fragments.

The second general method for gene synthesis utilizes polymerase to fill in single-stranded gaps in the annealed pairs of oligonucleotides. After the polymerase reaction, single-stranded regions of oligonucleotides become double-stranded, and after digestion with restriction endonuclease, can be cloned directly or used for further assembly of longer sequences by ligating different double-stranded fragments. This approach is relatively independent of the secondary structure of oligonucleotides; however, after the polymerase reaction, each segment must be cloned. The cloning step significantly delays the synthesis of long DNA fragments and greatly decreases the efficiency of the approach. Additionally, this approach can be used for only relatively small DNA fragments and requires restriction endonuclease recognition sites to be introduced into the sequence.

Thus, the major essential disadvantages of existing approaches for the synthesis of DNA is low efficacy and the requirement that synthesized DNA must be amplified by cloning procedures, or by the PCR, before use. The main problem with existing approaches is that the long polynucleotide must be assembled from relatively short oligonucleotides utilizing either inefficient chemical or enzymatic synthesis. The use of short oligonucleotides for the synthesis of long polynucleotides can cause many problems due to multiple interactions of complementary bases, as well as problems related to adverse secondary structure of oligonucleotides. These problems lower the efficiency and widespread use of existing synthetic approaches.

Therefore, there exists a great need for an efficient means to make synthetic DNA of any desired sequence. Such a method could be universally applied. For example, the method could be used to efficiently make an array of DNA having specific substitutions in a known sequence which are expressed and screened for improved function. The present invention satisfies these needs by providing an efficient and powerful method for the synthesis of DNA. The method is generally referred to as the Exchangeable Template Reaction (ETR).

SUMMARY OF THE INVENTION

The invention provides a method for the synthesis of DNA based on a cyclic mechanism of combining deoxyoligonucleotides comprising combining: (a) a series of unique single-stranded deoxypolynucleotides, each having a 5' sequence which, when in double-stranded form, can be enzymatically treated to form a unique 3' single-stranded protrusion for selective cyclic hybridization with another unique single-stranded deoxypolynucleotide of the series; (b) a unique deoxypolynucleotide having a 3' sequence which can selectively hybridize with one of the unique single-stranded deoxypolynucleotides of (a); (c) a polymerase which can direct the formation of double-stranded deoxypolynucleotides from the single-stranded deoxypolynucleotides; and (d) an enzyme which can form a unique single-stranded 3' protrusion from the double-stranded deoxypolynucleotides; under conditions which hybridize the unique single-stranded deoxypolynucleotides in a cyclic manner to form the DNA. Also provided is a kit comprising a series of unique synthesized single-stranded deoxypolynucleotides, each having a 5' sequence which, when in double-stranded form, can be enzymatically treated to form a unique 3' single-stranded protrusion for selective cyclic hybridization with another unique single-stranded deoxypolynucleotide of the series.

BRIEF DESCRIPTION OF THE FIGURES

FIG. 2-I shows the sequence of deoxyoligonucleotides designed for the ETR synthesis of a fragment corresponding to the HBV. Recognition sites for restriction endonucleases used for the ETR (BstXI) and for cloning (BgIII and ApaI) are indicated.

FIG. 2-II shows the stepwise description of the mechanism of the ETR for three deoxyoligonucleotides corresponding to the HBV genome.

FIG. 3-I shows the primary structure of the deoxyoligonucleotides corresponding to the 5' terminal region of the HCV nucleocapsid gene. Sites for restriction endonucleases used for the ETR (BstXI), for assembly of the gene (DdeI), and for cloning (NdeI) are shown.

FIG. 3-II shows a schematic representation of the ETR. Deoxyoligonucleotides are shown as solid lines. Points represent DNA polymerase synthesized regions of the double-stranded fragment. The upper strand consists of Oligo 1 and newly-synthesized sequences. The lower strand is composed of oligonucleotide sequences that remain after BstXI digestion and after synthesis of new sequences at the very 3' terminus of the strand. The order of the deoxyoligonucleotides involved in the reaction is indicated.

FIG. 4-I shows the primary structure of the deoxyoligonucleotides corresponding to the middle part of the HCV nucleocapsid gene.

FIG. 4-II shows a schematic representation of the ETR corresponding to the middle part of the HCV nucleocapsid gene.

FIG. 5-I shows the primary structure of the deoxyoligonucleotides corresponding to the 3' terminal region of the HCV nucleocapsid gene.

FIG. 5-II shows a schematic representation of the ETR corresponding to the 3' terminal region of the HCV nucleocapsid gene.

DETAILED DESCRIPTION OF THE INVENTION

Figure 1:
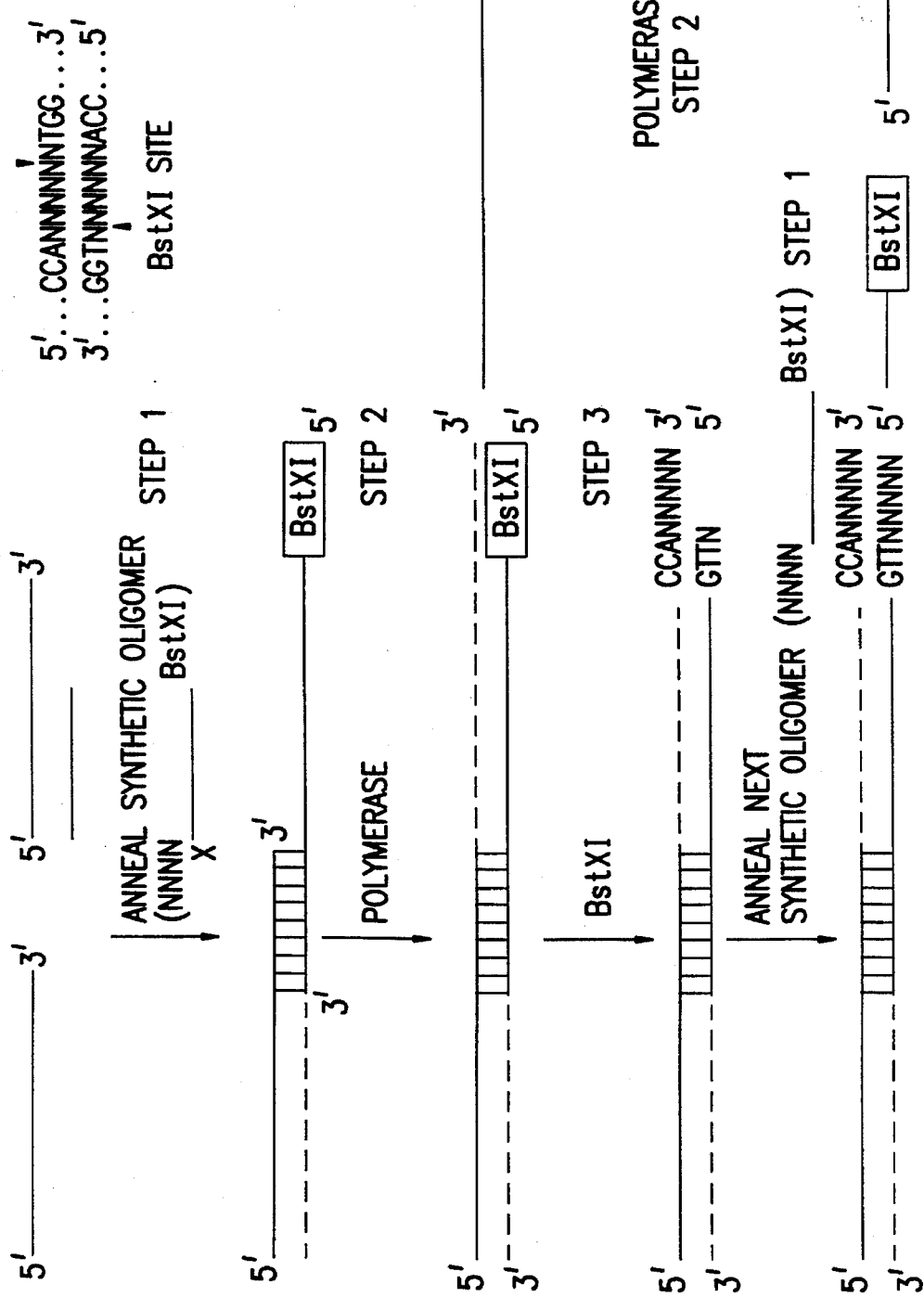
FIG. 1 is a schematic showing the general mechanism for the cyclic ETR.

Description of the Exchangeable Template Reaction (ETR) mechanism. The ETR is a method for the synthesis of long polynucleotide DNA fragments using short synthetic oligonucleotides as templates for DNA polymerase. The method is based on a cyclic mechanism involving three main components: (1) polymerase activity to synthesize double-stranded DNA, (2) enzymatic activity to create 3' terminal single-stranded regions, and (3) specifically designed synthetic deoxyoligonucleotides used as templates for the polymerase reaction. The critical step is the enzymatic creation of a 3' terminal single-stranded region at the "growing point" of the synthesizing polynucleotide chain, which is used for the complementary binding of the next oligonucleotide as a template to continue the polymerase reaction.

The order of oligonucleotide additions for each cycle is encoded in each 3' terminal sequence. At the 3' terminus of the growing DNA molecule a specific sequence of nucleotides can anneal with a complementary sequence of nucleotides from the synthetic oligonucleotide. Thus, it is possible to synthesize a long DNA fragment in one step by simply combining the entire set of deoxyoligonucleotides in one reaction tube containing all the required enzymatic activities and incubating the mixture at the optimal temperature and optimal buffer.

Each cycle begins with the complementary binding of the 3' terminal region of a synthetic oligonucleotide with the 3' protruding region of double-stranded DNA (step 1 in FIG. 1). After annealing, a DNA polymerase reaction occurs to create a second strand of DNA using the short synthetic oligonucleotide as a template for DNA polymerase (step 2 in FIG. 1). After polymerization is complete, the double-stranded DNA has been extended by the length of the synthetic oligonucleotide. To initiate the second round in the cycle of DNA synthesis, another enzymatic reaction occurs that creates a 3' protruding single-stranded region by removing several nucleotides from the 5' terminus leaving a 3' protrusion. This protrusion is used to anneal another short synthetic oligonucleotide (step 3 in FIG. 1).

Thus, this invention provides a method for the synthesis of DNA based on a cyclic mechanism of combining deoxyoligonucleotides comprising combining in any order:

(a) a series of unique single-stranded deoxypolynucleotides, each having a 5' sequence which, when polymerized to double-stranded form, can be enzymatically treated to form a unique 3' single-stranded protrusion for selective cyclic hybridization with another unique single-stranded deoxypolynucleotide of the series;

(b) a unique deoxypolynucleotide having a 3' sequence which can selectively hybridize with one of the unique single-stranded deoxypolynucleotides of (a);

(c) a polymerase which can direct the formation of double-stranded deoxypolynucleotides from the single-stranded deoxypolynucleotides; and (d) an enzyme which can form a unique single-stranded 3' protrusion from the double-stranded deoxypolynucleotides; under conditions which hybridize the unique deoxypolynucleotides in a cyclic manner and polymerize the hybridized deoxypolynucleotides to form the DNA.

"Cyclic" as used herein means a sequential hybridization in a regularly repeated order. Thus, as noted above, hybridization of deoxypolynucleotides (hereinafter "DPNTs") occurs only in a specified controlled order. For example, a series of DPNTs (two or more), each of which encodes a unique segment of a desired long DPNT, are synthesized. During the synthesis, the sequence of each DPNT is selected to produce, when later cleaved by an enzyme, a unique 3' protrusion which will hybridize with only one other member of the DPNT series. When the DPNTs are combined, only two of the DPNTs initially hybridize. Once this hybridization occurs, the sequence of the remaining synthesis is set. A polymerase utilizes the two hybridized DPNTs to form double strands. The appropriate enzyme then acts on the double-stranded DPNTs to form the unique 3' single-stranded protrusion. The next DPNT which hybridizes only with this unique 3' protrusion then hybridizes. Once this hybridization occurs, the polymerase again directs the synthesis of double strands. After the double strands are completed, the enzyme again produces a unique 3' single protrusion which was previously synthesized to hybridize only with the next unique DPNT. The sequence is then repeated the desired number of times.

This invention also provides hybridization and cleavage which proceeds in both directions, e.g., first hybridize DPNTs in the middle of the desired sequence with cleavage sites on both subsequently-formed ends. The selection of DPNTs and enzymes follows the procedure of unidirectional synthesis but enzyme sites on both ends of the double-stranded DNA are created.

Once a long DPNT is made by the above method, a new series of DPNTs can be added, each having a 5' sequence which, when in double-stranded form, can be enzymatically treated to form a unique 3' single-stranded protrusion for selective cyclic hybridization with another unique single-stranded DPNT of the series. This procedure can be repeated many times. The number of DPNTs in the reaction is only limited by undesired interference of hybridization. This can be avoided by creating unique 3' protrusions and hybridizing DPNTs which have minimal sequence similarity. Very long DPNTs including genes and entire genomes can thereby be synthesized by this method.

As can be appreciated from the above, the method works so long as a unique 3' single-stranded protrusion is formed by an enzymatically-treated hybridized unique DPNT. By "unique" is meant a nucleotide sequence on one DPNT which is absent on another DPNT so that selective hybridization can occur. The number of unique nucleotides necessary for selective hybridization depends on hybridization conditions. For example, for a 3' protrusion of four nucleotides, the optimal temperature of the reaction is about 37° C. This optimal temperature may be different if a different polymerase is utilized in the synthesis. This is true because different polymerases have different affinities to complementary complexes. Thermostable enzymes also have a rather high affinity to such complexes. A longer 3' protrusion should be more reactive and more specific in hybridization and utilize a higher annealing temperature. However, the single-stranded region must be of a size to avoid being involved in secondary structure formation. This region, to be effective in hybridization, should be represented in a single-stranded form at the reaction temperature. From this point of view, thermostable enzymes can be more effective in ETR because a higher reaction temperature can be utilized. Thus, very effective single-stranded terminal regions can be about 7–9 nucleotides long. For such lengths it is routine to find conditions to maintain single-stranded form. Specific complementary complexes between DPNTs can be effectively organized at higher temperatures, which decreases the possibility of improper complex formation. The optimal temperature for the 7–9 nucleotide 3' protrusion may be around 55°–65° C., the optimal temperature for the activity of thermostable polymerases. Thus, a preferred range of 3' protrusion length is about 3–12 nucleotides. Longer protrusions can be made and routinely tested by the methods described in the Experimental section to optimize length and conditions for a particular system.

The precise 5' sequence of a member of the series will depend on the desired sequence for the ultimate DNA and the type of enzyme utilized to form the protrusion. Thus, once an ultimate desired sequence is selected, a 5' sequence is synthesized which corresponds to the desired sequence and which will either be cleaved or exposed such that the desired sequences remain and the undesired sequences, if any, are removed prior to hybridization of the next member of the series. For example, if a restriction endonuclease is utilized, it must cleave in such a way that unique sequences for each member of the series to be hybridized are produced. BstXI, as described in detail in the Experimental section, provides one example of such a restriction endonuclease because the endonuclease allows for four unique nucleotides to be synthesized in each member of the series which remains after cleavage.

Because of the unique nature of the 5' sequence which is treated to produce the unique 3' protrusion, the members of the series of DPNTs must be synthesized if a restriction endonuclease is utilized, for example with a DNA synthesizer. Since the DPNT which starts the hybridization can hybridize directly with the second DPNT, it is not affected by the enzymatic treatment. Therefore, the first unique DPNT can be obtained, if desired, by means other than synthesis and can be single- or double-stranded. For example, the DPNT can be a fragment excised from natural DNA, e.g. plasmid, phage genome, or viral genome by restriction endonucleases. Likewise, the fragment can be obtained by specific amplification using PCR. PCR fragments are more suitable because terminal sequences of the amplified fragment can be easily modified with primers used for amplification with the introduction of desirable nucleotide modifications, including artificially synthesized non-natural derivatives of nucleotides. Any suitable number of nucleotides sufficient for efficient hybridization under the selected conditions can be utilized for this initial hybridization.

This unique synthesis-initiating DPNT, which begins synthesis by providing a template for hybridization of the second DPNT from the series, can be bound to a solid support for improved efficiency. The solid phase allows for the efficient separation of the synthesized DNA from other components of the reaction. Different supports can be applied in the method. For example, supports can be magnetic latex beads or magnetic control pore glass beads. Being attached to the first DPNT, these beads allow the desirable product from the reaction mixture to be magnetically separated. Binding the DPNT to the beads can be accomplished by a variety of known methods, for example carbodiimide treatment (Gilham, *Biochemistry* 7:2809–2813 (1968); Mizutani and Tachbana, *J. Chromatography* 356:202–205 (1986); Wolf et al., *Nucleic Acids Res.* 15:2911–2926 (1987); Musso, *Nucleic Acids Res.* 15:5353–5372 (1987); Lund et al., *Nucleic Acids Res.* 16:10861–10880 (1988)). The DPNT attached to the solid phase is the primer for synthesis of the whole DNA molecule. Synthesis can be accomplished by addition of sets of compatible oligonucleotides together with enzymes. After the appropriate incubation time, unbound components of the method can be washed out and the reaction can be repeated again to improve the efficiency of each oligonucleotide to be utilized as a template. Alternatively, another set of oligonucleotides can be added to continue the synthesis This "set principle," barely applicable to solution synthesis, turns the method into a very powerful method for the synthesis of a long DNA molecule that is not possible with any other methods.

Solid phase, to be efficiently used for the synthesis, can contain pores with sufficient room for synthesis of the long DNA molecules. The solid phase can be composed of material that cannot non-specifically bind any undesired components of the reaction. One way to solve the problem is to use control pore glass beads appropriate for long DNA molecules. The initial primer can be attached to the beads through a long connector. The role of the connector is to position the primer from the surface of the solid support at a desirable distance.

Any polymerase which can direct the synthesis of double strands from partially hybridized single strands is appropriate. Suitable polymerases, for example, may include Taq polymerase, large fragments of *E. coli* DNA polymerase I, DNA polymerase of T7 phase. The optimal conditions of the polymerization vary with the type of polymerase used. Likewise, the optimal polymerase can vary with the conditions necessary for the synthesis (Bej et al., *Crit. Rev. Biochem. Mol. Biol.* 26(3–4): 301–334 (1991); Tabor and Richardson, *Proc. Natl. Acad. Sci. USA.* 86:4076–4080 (1989); Petruska et al., *Proc. Natl. Acad. Sci. USA* 85:6252–6256 (1988)). One example of an enzyme capable of removing several nucleotides from the 5' terminus is the restriction endonuclease BstXI. This restriction endonuclease is compatible with ETR for the following reasons: (1) a 3' protrusion is produced, (2) the single-stranded 3' protrusion does not have any sequence restrictions, and (3) after cleavage the restriction site cannot be restored by the interaction of the next synthetic oligonucleotides.

While the Experimental section is directed towards the use of BstXI, the discovery is the production of a unique 3' protrusion however it is obtained. Therefore, in the subject method, any enzyme can be utilized which can form a unique 3' protrusion from double-stranded DNA. Other presently known enzymes useful in the method include 5' exonucleases specific for double-stranded DNA, such as the exonuclease of T7 and lambda phage, and an enzyme of DNA recombination, such as recA.

The method utilizing a 5' exonuclease specific for double-stranded DNA can be performed as follows: oligonucleotides to be used in the reaction as templates for polymerase reaction are chemically modified at a defined point to prevent T7 exonucleases from jumping over the modified nucleotides. For example, oligonucleotide phosphorodithioates can be utilized using methods described in Caruthers, *Nucl. Acids Symp. Ser.* 21:119–120 (1989). As described above, polymerase first fills gaps in hybridized DPNTs. When the reaction is finished, the exonuclease of the T7 starts cutting double-stranded DNA beginning from the 5' end (the opposite 5' end should be modified or attached to solid phase to prevent cleavage from the end). This reaction goes until the modified position where it stops. The 3' protrusion created by the exonuclease activity can then be used for hybridization with the next oligonucleotide in the cycle reaction. T7 is well known to have a relatively strong preference for double-stranded DNA (Kerr and Sadowski, *J. Biol. Chem.* 247:311–318 (1972); Thomas and Olivera, *J. Biol. Chem.* 253:424–429 (1978); Shon et al., *J. Biol. Chem.* 25:13823–13827 (1982)).

Another double-stranded specific exonuclease is encoded by lambda phage (Sayers et al., *Nucleic Acids Res.* 16:791–802 (1988)). This enzyme can also be utilized in the method.

The main advantage of these exonucleases is the possibility of creating a single-stranded 3' protrusion of any necessary size to allow the use of higher temperatures in the reaction. Additionally, because the exonuclease recognizes any blunt end, its use eliminates the need to synthesize DPNT having a restriction site when polymerized to double-stranded form.

The method can also be performed utilizing an enzyme of DNA recombination. It is known that recA can replace one strand of double-stranded DNA, in a strong sequence-specific manner, with a single-stranded DNA from solution creating D-loop structures (Cox and Lehman, *Ann. Rev. Biochem.* 56:229–262 (1987); Tadi-Laskowski et al., *Nucleic Acids Res.* 16:8157–8169 (1988); Hahn et alo, *J. Biol. Chem.* 263:7431–7436 (1988)). In this modification of the method, DPNTs are combined in one reaction with polymerase and recA. Polymerase fills single-stranded gaps and recA replaces the terminal region of one of the strands of double-stranded DNA with a single-stranded DPNT from solution which provides the polymerase with a new template. An advantage of the reaction is strong specificity of the hybridization which is due to enzymatic support. In any other variations of the method, for example with restriction endonucleases and exonucleases, the hybridization is the only step without enzymatic support. While restriction endonucleases and exonucleases can only create a 3' protrusion, recA can create a single-stranded region at the ends of double-stranded DNA and anneals oligonucleotides to the 3' protrusion.

The invention also provides various novel compositions used in the invention. Provided is a kit comprising a series of unique synthesized single-stranded DPNTs, each having a 5' sequence which, when polymerized to double-stranded form, can be enzymatically treated to form a unique 3' single-stranded protrusion for selective cyclic hybridization with another unique single-stranded DPNT of the series. The DPNTs can exist in lyophilized form or in a suitable carrier such as saline. The kit can further comprise a unique DPNT having a 3' sequence which can selectively hybridize with one of the series of unique single-stranded DPNTs. The kit can still further comprise a polymerase which can direct the formation of double-stranded polynucleotides from the single-stranded DPNTs. Finally, the kit can comprise an enzyme which can form a unique single-stranded protrusion from the double-stranded DPNTs.

The invention also provides an automated synthesizer programmed to perform the method of claim 1 and remove undesired components. This synthesizer can be programmed to perform repeat cycles of the synthesis.

EXPERIMENTAL

MATERIALS AND METHODS

Deoxyoligonucleotides were synthesized using an automatic synthesizer (Applied Biosystem Model 380B, Foster City, Calif.) and purified by polyacrylamide gel electrophoresis (PAGE) in 10% polyacrylamide in TBE buffer (0.045M Tris-borate, pH 8.3, containing 0.001M EDTA and 7M urea). Oligonucleotides were recovered from the gel by electroelution.

The ETR was carried out at 37° C. for 0.5–5 hrs. in a volume of 50 µl of 10 mM Tris-HCl buffer, pH 7.9, containing 10 mM MgCl; 50 mM NaCl; 1 mM DTT; 0.25 mM each of dATP, dGTP, dTTP, and dCTP (Pharmacia-LKB, Uppsala, Sweden); 5 units of native Taq DNA polymerase (Cetus Corp., Emeryville, Calif.); 30 units of BstXI (New England BioLabs, Beverly, Mass.); and 0.5–100 pmol of each deoxyoligonucleotide. Analysis of the reaction course was accomplished by utilizing one of the deoxyoligonucleotides without a BstXI site radiolabeled with [gamma-$^{32}$P] ATP in 50 mM Tris-HC1, pH 7.6, containing 10 mM MgCl, 5 mM DTT, 10 µCI [gamma-$^{32}$P] ATP (5,000 Ci/mmole, New England Nuclear, Wilmington, Del.), and 10–20 pmol of oligonucleotide. After the completion of the ETR, the products were analyzed by PAGE in 8% polyacrylamide containing 8M urea, and the specific products were revealed by autoradiography.

RESULTS

Verification of ETR using BstXI. The BstXI is a commercially available endonuclease that satisfies the requirements stated above. The major drawback of this enzyme is that it produces only a 4 nucleotide single-stranded 3' protrusion for annealing to the next oligonucleotide. We anticipated that this short protrusion may lower the overall efficiency of the ETR relative to the use of an exonuclease, which would yield a much longer protrusion. Nevertheless, we decided to explore this approach since it represented the easiest way to verify the cyclic mechanism involved in the synthesis of DNA by the ETR. Accordingly, four sets of oligonucleotides were designed and synthesized (FIGS. 2–5).

Set 1. Synthesis of a DNA fragment of the hepatitis B virus (HBV) genome. One of the most powerful applications of synthetic DNA fragments is in site-specific mutagenesis of DNA, especially if the introduction of multiple mutations is desired in a long sequence. Using ETR, a DNA fragment corresponding to the sequence encoding the terminal protein of the HBV genome was synthesized and modified by changing the nucleotide sequence of one of the deoxynucleotides. This fragment was created from three deoxynucleotides (FIG. 2-I) (SEQ ID Nos: 2–4) and synthesized by the ETR as shown in FIG. 2-II (SEQ ID Nos. 5–9). All three deoxynucleotides were combined in one tube with Taq DNA polymerase and BstXI in the presence of DPNTs. Different relative concentrations of the oligonucleotides were used in the reaction. Deoxynucleotide A (SEQ ID No: 2) was radiolabeled. The concentrations of deoxynucleotide A and B (SEQ ID No: 3) were fixed at 1 pmol, while the concentration of deoxynucleotide C(SEQ ID No: 4) was used at 1 pmol, 10 pmol, and 100 pmol. Reactions containing 10 pmol and 100 pmol of C were more efficient than reactions containing 1 pmol of C with no significant differences in efficiency between reactions containing 10 pmol and 100 pmol. When the amount of B was increased to 10 pmol, there was no improvement in the efficiency of synthesizing a full-size fragment. Although a 10-fold molar excess of B and C over labeled A did not improve the efficiency of the ETR, these conditions did, however, make the reaction more reproducible. In all subsequent experiments, at least a 10-fold molar excess of the unlabeled to labeled oligonucleotides were used for monitoring the reactions. In control experiments without B or C, no DNA fragment of the expected size was found. Reactions were carried out at constant temperatures of 4° C., 10° C., 20° C., 37° C., 42° C., and 65° C. The best yield was obtained at 37° C. No full-size fragment was obtained at 4° C., 10° C., or 65° C. Only a dimer of A and B was found at these temperatures. At 37° C, a full-size fragment was obtained after a 5 min. incubation. After a 5 h. incubation, the full-size fragment gave a strong band by autoradiography. This fragment was cleaved with restriction endonucleases, and amplified by the PCR, which produced a fragment of the correct size measured by electrophoresis.

In experiments using radiolabeled deoxynucleotide A, a full-size fragment was identified after electrophoresis under denaturating conditions. When radiolabeled deoxynucleotide C was used, no synthesis occurred. This result was reproducible and suggested that only A can initiate the polymerase synthesis of full-size DNA fragments using B and C as templates. The double-stranded DNA product of the ETR contains a non-interrupted strand synthesized by the polymerase reaction and primed with A, and a second strand with nicks between the other oligonucleotides that participated in the reaction as templates for the polymerase reaction. These nicks can be repaired with DNA ligase. Alternatively, the DNA fragments can be used directly for cloning, amplified by the PCR, or treated with other DNA-modifying enzymes such as restriction endonucleases.

Set 2. Synthesis of the DNA fragments encoding for the nucleocapsid protein of the hepatitis C virus (HCV). The DNA sequence encoding the HCV nucleocapsid protein was divided into 3 fragments. Each fragment was synthesized separately by the ETR (FIGS. 3–5). The first fragment was synthesized from 5 deoxynucleotides (FIG. 3) (SEQ ID No: 10–14), the second fragment from 3 (FIG. 4) (SEQ ID Nos: 15–17), and the third from 4 deoxynucleotides (FIG. 5) (SEQ ID Nos: 18–21). All reactions were carried out as described above. The longest synthesized fragment contained 228 base pairs (bp). The yield of full-size fragments was estimated to be approximately 5–10%.

Different buffers were tested (Table 1) for the ETR using oligonucleotides to synthesize the first segment of the gene (FIG. 3). Buffer NEB3 is the optimal buffer for BstXI, whereas the various Taq buffers are optimal for Taq DNA polymerase. The best result for the ETR reaction utilized, however, was obtained with buffers NEB2 and NEB4.

Both BstXI and Taq polymerase have high optimal temperature conditions. Because of the short single-stranded protrusion formed by BstXI, however, the ETR was found to be optimal at 37° C. rather than the optimal temperatures for these enzymes.

For the ETR synthesis of the first segment, corresponding to the HCV nucleocapsid gene (core protein), the relative concentrations of the deoxynucleotides was 1:4:20:40:60. When the relative concentrations were changed to 1:1:20:40:60, the rate of ETR was changed as well. At 1:4:20:40:60 relative concentrations of oligonucleotides, the full-size fragment could be detected after a 3 hr. incubation period at 37° C. in NEB2. At the 1:1 relative concentrations of deoxynucleotides 1 and 2, the fragment was synthesized in detectable amounts after only a 30 min. incubation period.

Each of the three fragments synthesized by the ETR was purified by PAGE and amplified by the PCR. Amplified products were digested with the appropriate restriction endonuclease and treated with DNA ligase. The whole gene was amplified again and analyzed by restriction endonuclease mapping. The amplified product was inserted into an expression vector under the control of the T7 promoter. Briefly, this DNA fragment and vectorp TS7 (especially constructed for the expression of the HCV core protein) were cleaved with NdeI and HindIII. After removal of the enzymes these DNA components were mixed and treated with DNA ligase. The ligation mixture was used to transform *E. coli* that produce T7 RNA polymerase. Transformed *E. coli* cells expressed an immunologically active product detected by Western Blot analysis using sera previously shown reactive for HCV anticore activity (MATRIX, Abbott Laboratories, Abbott Park, Ill.). In addition, the expressed product possessed the correct molecular weight based on SDS-PAGE analysis. Thus, all three segments corresponding to the HCV nucleocapsid gene were correctly synthesized by the ETR.

The fragment was then sequenced using standard techniques. The sequence confirmed the success of the ETR. The sequence was found to be exactly as designed. DNA synthesis utilizing ETR is a method of producing DNA of precise fidelity.

It should be understood that the foregoing relates only to preferred embodiments of the present invention and that numerous changes and modifications may be made therein as described in the following claims.

What is claimed is:

1. A method for the synthesis of DNA based on a cyclic mechanism of combining deoxypolynucleotides comprising admixing:

(a) a plurality of unique single-stranded deoxypolynucleotides, wherein each unique deoxypolynucleotide has one or more copies and a 5' sequence which, when the deoxypolynucleotide is in double-stranded form, can be enzymatically treated to form a unique 3' single-stranded protrusion for selective cyclic hybridization of the enzymatically-treated double-stranded deoxypolynucleotide with another unique single-stranded deoxypolynucleotide;

(b) a unique single-stranded deoxypolynucleotide having a 3' sequence which can selectively hybridize with only one of the unique single-stranded deoxypolynucleotides of (a);

(c) a polymerase which can direct the formation of double-stranded deoxypolynucleotides from the hybridization product of the unique single-stranded deoxypolynucleotides of (a) and (b); and (d) a single enzyme which forms a unique single-stranded 3' protrusion from each unique member of the double-stranded deoxypolynucleotides formed by the polymerization of the single-stranded deoxypolynucleotides of (a) and (b) with the polymerase of (c);

under conditions which (1) hybridize the unique single-stranded deoxypolynucleotide of (b) with the first member of the plurality of the unique single-stranded deoxypolynucleotides of (a), (2) polymerize the hybridized deoxypolynucleotides to form a double-stranded DNA and (3) Can form the unique 3' single-stranded protrusion of step (d) for cyclic hybridization, polymerization and unique 3' single-stranded protrusion formation with the remaining members of the plurality of unique single-stranded deoxypolynucleotides of (a) in a single reaction mixture.

2. The method of claim 1, further comprising combining the DNA resulting from the synthesis based on the cyclic mechanism of combining deoxypolynucleotides of claim 1 with a second plurality of unique synthesized single-stranded deoxypolynucleotides, wherein each unique deoxypolynucleotide has one or more copies and a 5' sequence which, when the deoxypolynucleotide is in double-stranded form, can be enzymatically treated to form a unique 3' single-stranded protrusion for selective cyclic hybridization of the enzymatically-treated double-stranded deoxypolynucleotide with another unique single-stranded deoxypolynucleotide of the second plurality; under conditions which hybridize the unique single-stranded deoxypolynucleotides in a cyclic manner to the DNA resulting from the synthesis based on the cyclic mechanism of combining deoxypolynucleotides of claim 1.

3. The method of claim 2, repeated a plurality of times.

4. The method of claim 1, wherein the unique single-stranded deoxypolynucleotides are synthesized.

5. The method of claim 1, wherein each of the unique single-stranded deoxypolynucleotides encodes a unique portion of a gene.

6. The method of claim 1, wherein the plurality of unique single-stranded deoxypolynucleotides comprises at least three deoxypolynucleotides.

7. The method of claim 1, wherein the 5' sequence, when in double-stranded form, can be enzymatically cleaved with a restriction endonuclease to form a 3' protrusion.

8. The method of claim 7, wherein the 5' sequence comprises (SEQ ID No: 1)

5'CCANNNNNNTGG 3'

3'GGTNNNNNNACC 5' wherein N is any nucleotide.

9. The method of claim 1, wherein the 5' sequence, when in double-stranded form, can be enzymatically cleaved by a 5' exonuclease specific for double-stranded deoxypolynucleotides to form a 3' protrusion.

10. The method of claim 1, wherein the deoxypolynucleotide of (b) is bound to a solid support prior to combining with the deoxypolynucleotides of (a).

11. The method of claim 10, wherein solid support is comprised of beads.

12. The method of claim 11, wherein the beads are solid phase controlled pore glass.

13. The method of claim 12, wherein the beads are coated with glycerol.

14. The method of claim 11, wherein the beads are coated with avidin.

15. The method of claim 14, wherein the avidin beads are bound to biotin.

16. The method of claim 1, wherein the combining is performed substantially simultaneously.

17. The method of claim 1, wherein the polymerase is Taq polymerase.

18. The method of claim 1, wherein the enzyme is a restriction endonuclease.

19. The method of claim 18, wherein the restriction endonuclease is BstxI.

20. The method of claim 1, wherein the enzyme is a 5' exonuclease specific for double-stranded deoxypolynucleotides.

21. The method of claim 20, wherein the exonuclease is selected from the group consisting of the exonuclease of T7 and lambda phage.

22. The method of claim 1, wherein the enzyme is an enzyme of DNA recombination.

23. The method of claim 22, wherein the enzyme of DNA recombination is recA.

24. A kit comprising (1) a plurality of unique synthesized single-stranded deoxypolynucleotides, wherein each unique synthesized deoxypolynucleotide has one or more copies and a 5' sequence which, when the synthesized deoxypolynucleotide is in double-stranded form, can be enzymatically treated to form a unique 3' single-stranded protrusion for selective cyclic hybridization of the enzymatically treated double-stranded deoxypolynucleotide with another unique single-stranded deoxypolynucleotide and (2) an enzyme selected from the group consisting of exonuclease and restriction endonuclease, which can form a unique single-stranded 3' protrusion from each of the double-stranded deoxypolynucleotides formed by the polymerization of the hybridized unique single-stranded deoxypolynucleotides.

25. The kit of claim 24, further comprising a unique deoxypolynucleotide having a 3' sequence which can selectively hybridize with one of the unique single-stranded deoxypolynucleotides.

26. The kit of claim 24, further comprising a polymerase which can direct the formation of double-stranded polynucleotides from the single-stranded deoxypolynucleotides.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

CCANNNNNT GG    1 2

( 2 ) INFORMATION FOR SEQ ID NO:2:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
CCCAGATCTC AATCTCGGGA ATCTCAATGT TAGTATTCCT TGGACTCATA AGGTGGGAA          59
```

( 2 ) INFORMATION FOR SEQ ID NO:3:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CCCCCACCAC TCTGGATTAA AGATAGGTAC TGTAGAGGAA AAAAGCGCCG TAAAGTTTCC          60
CACCTTAT                                                                  68
```

( 2 ) INFORMATION FOR SEQ ID NO:4:

( i ) SEQUENCE CHARACTERISTICS:
        ( A ) LENGTH: 79 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CCCGGGCCCA CAAATTGTTG ACACCTATTA ATAATGTCCT CTTGTAAATG AATCTTAGGA          60
AAGGAAGGAG TTTGCCACT                                                      79
```

( 2 ) INFORMATION FOR SEQ ID NO:5:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

```
CCCAGATCTA TAAGGTGGGA A                                                   21
```

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

```
CCCCCACCAC TCTGGTTCCC ACCTTAT                                             27
```

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

CCCAGATCTA TAAGGTGGGA ACCAGAGTGG TGGGGG        36

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

CCCAGATCTA TAAGGTGGGA ACCAGAGTG        29

(2) INFORMATION FOR SEQ ID NO:9:

(i) SEQUENCE CHARACTERISTICS:
        (A) LENGTH: 38 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

CCCGGGCCCC ACTCTGGTTC CCACCTTATA GATCTGGG        38

(2) INFORMATION FOR SEQ ID NO:10:

(i) SEQUENCE CHARACTERISTICS:
        (A) LENGTH: 76 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CCCCATATGA GCACGATTCC TAAACCACAA AGAAAAACCA AACGTAACAC CAATCGACGA        60

CCACAAGATG TAAAGT        76

(2) INFORMATION FOR SEQ ID NO:11:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

CCCCCACCTC CGTGGAAGCA AATAGACTCC ACCAACGATC TGACCGCCAC CCGGGAACTT        60

TACATCTTG        69

(2) INFORMATION FOR SEQ ID NO:12:

( i ) SEQUENCE CHARACTERISTICS:
    ( A ) LENGTH: 45 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

```
CCCCCATCTT CCTGGTCGCG CGCACACCCA ACCTAGGTCC CCTCC                    45
```

( 2 ) INFORMATION FOR SEQ ID NO:13:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

```
CCCCCAACCT CGTGGTTGCG AGCGCTCGGA AGTCTTC                             37
```

( 2 ) INFORMATION FOR SEQ ID NO:14:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

```
CCCCCTCAGG CCGACGCACT TTAGGGATAG GCTGTCGTCT ACCTC                    45
```

( 2 ) INFORMATION FOR SEQ ID NO:15:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

```
CCCCCTGAGG GCAGGACCTG GGCTCAACCC GGTTACCCCT GGCCCCTCTA TGGCAATGAG    60
GGCTGCGGGT GGGCG                                                    75
```

( 2 ) INFORMATION FOR SEQ ID NO:16:

( i ) SEQUENCE CHARACTERISTICS:
        ( A ) LENGTH: 71 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

```
CCCCCAGATC AGTGGGTCCC CAACTCGGTC GAGAGCCGCG GGGAGACAGG AGCCATCCCG    60
CCCACCCGCA G                                                        71
```

( 2 ) INFORMATION FOR SEQ ID NO:17:

(i) SEQUENCE CHARACTERISTICS:
  (A) LENGTH: 46 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:17:

CCCATCGATG ACCTTACCCA AATTTCGCGA CCTACGTCGC GGATCA    46

(2) INFORMATION FOR SEQ ID NO:18:

(i) SEQUENCE CHARACTERISTICS:
    (A) LENGTH: 57 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:18:

CCCATCGATA CCCTCACGTG CGGCTTCGCC GACCTCATGG GGTACATACC GCTCGTC    57

(2) INFORMATION FOR SEQ ID NO:19:

(i) SEQUENCE CHARACTERISTICS:
    (A) LENGTH: 62 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:19:

CCCCCAACTC CATGGGCAAG GGCTCTGGCG GCACCTCCAA GAGGGGCGCC GACGAGCGGT    60
AT    62

(2) INFORMATION FOR SEQ ID NO:20:

(i) SEQUENCE CHARACTERISTICS:
    (A) LENGTH: 79 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:20:

CCCCCAGGAA GATGGAGAAA GAGCAACCAG GAAGGTTTCC TGTTGCATAA TTGACGCCGT    60
CTTCTAGAAC CCGTACTCC    79

(2) INFORMATION FOR SEQ ID NO:21:

(i) SEQUENCE CHARACTERISTICS:
    (A) LENGTH: 73 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:21:

CCCAAGCTTT TAGTTTCGAA CTTGGTAGGC TGAAGCGGGC ACAGTCAGGC AAGAGAGCAG    60
GGCCAGAAGG AAG    73